United States Patent
Yang (10) Patent No.: US 9,382,330 B2
(45) Date of Patent: Jul. 5, 2016

(54) PDIA4, TARGET OF CYTOPILOYNE DERIVATIVES, FOR TUMOR DIAGNOSIS AND TREATMENT

(75) Inventor: Wen-Ching Yang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 982 days.

(21) Appl. No.: 13/103,845

(22) Filed: May 9, 2011

(65) Prior Publication Data

US 2011/0280809 A1 Nov. 17, 2011

Related U.S. Application Data

(60) Provisional application No. 61/333,060, filed on May 10, 2010.

(51) Int. Cl.

| | |
|---|---|
| *A61K 31/704* | (2006.01) |
| *C07K 16/40* | (2006.01) |
| *A61K 31/00* | (2006.01) |
| *A61K 31/337* | (2006.01) |
| *A61K 31/36* | (2006.01) |
| *A61K 31/4188* | (2006.01) |
| *A61K 31/713* | (2006.01) |
| *A61K 38/12* | (2006.01) |
| *A61K 45/06* | (2006.01) |
| *G01N 33/574* | (2006.01) |

(52) U.S. Cl.
CPC ............... *C07K 16/40* (2013.01); *A61K 31/00* (2013.01); *A61K 31/337* (2013.01); *A61K 31/36* (2013.01); *A61K 31/4188* (2013.01); *A61K 31/704* (2013.01); *A61K 31/713* (2013.01); *A61K 38/12* (2013.01); *A61K 45/06* (2013.01); *G01N 33/57407* (2013.01); *G01N 33/57484* (2013.01); *G01N 2333/99* (2013.01)

(58) Field of Classification Search
None
See application file for complete search history.

(56) References Cited

U.S. PATENT DOCUMENTS

2003/0152565 A1  8/2003  Bartorelli

FOREIGN PATENT DOCUMENTS

WO  WO 2010/004214  1/2010

OTHER PUBLICATIONS

Burdine, L. et al, Target Identification in Chemical Genetics: The (Often) Missing Link, May 2004, Chemistry & Biology, vol. 11, pp. 593-597.
Carbone, D. L. et al., Cysteine Modification by Lipid Peroxidation Products Inhibits Protein Disulfide Isomerase, Chem. Res. Toxicol., Mar. 18, 2005, pp. 1324-1331.
Chang, C. et al, Cytopiloyne, a Polyacetylenic Glucoside, Prevents Type 1 Diabetes in Nonobese Diabetic Mice, 2007, The Journal of Immunology 178, pp. 6984-6993.
Chang, J. et al, Antileukemic Activity of *Bidens pilosa* L. var. minor (Blume) Sherff and Houttuynia cordata Thunb, American Journal of Chinese Medicine, 2001 vol. 29, No. 2, pp. 303-312.
Chiang, Y. et al, Cytopiloyne, a novel polyacetylenic glucoside from Bidens pilosa, functions as a T helper cell modulator, Oct. 2006, Journal of Ethnopharmacology 110, pp. 532-538.
Chiang, S. et al, Flavonoids, centaurein and centaureidin, from *Bidens pilosa*, stimulate IFN-γ expression, Mar. 2007, Journal of Ethnopharmacology 112 (2007) 232-236.
Ciaffi, M. et al, Cloning and characterization of wheat PDI (protein disulfide isomerase) homoeologous genes and promoter sequences, 2006, Gene 366, pp. 209-218.
Dembitsky, V. M., Anticancer Activity of Natural and Synthetic Acetylenic Lipids, Oct. 2006, Lipids 41, pp. 883-924.
Ellerman, D. et al, A Role for Sperm Surface Protein Disulfide Isomerase Activity in Gamete Fusion: Evidence for the Participation of ERp57, Jun. 2006, Developmental Cellular 10, pp. 831-837.
Farquhar, R. et al, Protein disulfide isomerase is essential for viability in *Saccharomyces cerevisiae*, Gene, 108, Jun. 1991, Gene, 108 pp. 81-89.
Feng, W. et al, The Asparagine-linked Oligosaccharides of the Human Chorionic Gonadotropin B Subunit Facilitate Correct Disulfide Bond Pairing, The Journal of Biological Chemistry, May 19, 1995 vol. 270, No. 20, pp. 11851-11859.
Garbi, N. et al, Impaired assembly of the major histocompatibility complex class I peptide-loading complex in mice deficient in the oxidoreductase ERp57, Nature Immunology, Jan. 2006, vol. 7, No. 1, pp. 93-102.
Gillis, S. et al, Biochemical and Biological Characterization of Lymphocyte Regulatory Molecules, J. Exp. Med., Dec. 1980, vol. 152, pp. 1709-1719.
Goplen, D. et al, Protein Disulfide Isomerase Expression is Related to the Invasive Properties of Malignant Glioma, Oct. 15, 2006, Cancer Res. 66 pp. 9895-9902.
Grabher, C. et al, Notch 1 activation in the molecular pathogenesis of T-cell acute lymphoblastic leukaemia, May 2006, Nature Reviews Cancer, vol. 6, pp. 347-359.
Kuznetsov, G. et al, Several Endoplasmic Reticulum Stress Proteins, Including ERp72, Interact with Thyroglobulin during Its Maturation, Jul. 15, 1994, The Journal of Biological Chemistry vol. 269, No. 37, pp. 22990-22995.
Li, X. et al, Competitive Inhibition of a Set of Endoplasmic Reticulum Protein Genes (GRP78, GRP94, and ERp72) Retards Cell Growth and Lowers Viability after Ionophore Treatment, Molecular and Cellular Biology, Apr. 1991, vol. 11, No. 7, pp. 3446-3453.

(Continued)

*Primary Examiner* — Michele K Joike
(74) *Attorney, Agent, or Firm* — Hsiu-Ming Saunders; Intellectual Property Connections, Inc.

(57) ABSTRACT

Methods of diagnosing cancer that are based in part on the findings that Pdia4 promotes cell growth, cell proliferation, and cell cycle are disclosed herein. Methods of using microvessel density as a surrogate marker and reducing tumor microvessel density in a subject are also enclosed herein.

16 Claims, 5 Drawing Sheets

(56) References Cited

OTHER PUBLICATIONS

Lovat, P. et al, Increasing Melanoma Cell Death Using Inhibitors of Protein Disulfide Isomerases to Abrogate Survival Responses to Endoplasmic Reticulum Stress, Jul. 2008, Cancer Res. 68, pp. 5363-5369.

Maattanen, P. et al, ERp57 and PDI: multifuncitional protein disulfide isomerases with similar domain architectures but differing substrate-partner associations, Biochem. Cell Biol. 84, pp. 881-889.

Manukyan, D. et al, Protein disulfide isomerase as a trigger for tissue factor-dependent fibrin generation, Thrombosis Research 2008, 122 Suppl 1, pp. S19-S22.

Meunier, L. et al., A Subset of Chaperones and Folding Enzymes Form Multiprotein Complexes in Endoplasmic Reticulum to Bind Nascent Proteins, Molecular Biology of the Cell, Dec. 2002, vol. 13, pp. 4456-4469.

Naguleswaran, A. et al, Neospora caninum protein disulfide isomerase is involved in tachyzoite-host cell interatction, Jun. 2005, International Journal for Parasitology 35, pp. 1459-1472.

Ni, M. et al, ER chaperones in mammalian development and human diseases, FEBS Letters 581, Apr. 2007, pp. 3641-3651.

Norgaard, P. et al, Functional Differences in Yeast Protein Disulfide Isomerases, Feb. 5, 2001, The Journal of Cell Biology, vol. 152, No. 3, pp. 553-562.

Ou, W. et al, Role of protein disulfide isomerase and other thiol-reactive proteins in HIV-1 envelope protein-mediated fusion, 2006 Virology 350, pp. 406-417.

Parker, Ronald. et al, Identification of TFII-1 as the Endoplasmic Reticulum Stress Response Element Binding Factor ERSF: Its Autoregulation by Stress and Interaction with ATF6, Molecular and Cellular Biology, May 2001, pp. 3220-3233.

Satoh, M. et al., Functional characterization of 3 thioredoxin homology domains of ERp72, Cell Stress & Chaperones 2005, vol. 10, pp. 278-284.

Severino, A. et al, Identification of Protein Disulfide Isomerase as a Cardiomyocyte Survival Factor in Ischemic Cardiomyopathy, Journal of the American College of Cardiology, 2007, vol. 50, No. 11, pp. 1029-1037.

Shun, Shi. et al, Synthesis of Naturally Occurring Polyynes, Chem. Int. Ed. Engl. 2006, 45, pp. 1034-1057.

Spring, D. R., Chemical genetics to chemical genomics: small molecules offer big insights, Chemical Society Reviews, Feb. 2005, 34, pp. 472-482.

Sundararajan, P. et al, Studies of anticancer and antipyretic activity of Bidens pilosa whole plant, 2006, African Health Sciences 6(1), pp. 27-30.

Tiscornia, G., Singer, O., and Verma, I. M. (2006) Nature Protocols, vol. 1 No. 1, 20061(1), 241-245.

Turano, C. et al, Proteins of the PDI Family: Unpredicted Non-ER Locations and Functions, 2002, Journal of Cellular Physiology 193, pp. 154-163.

Vandenbroeck, K. et al, Multi-chaperone complexes regulate the folding of interferon-Y in the endoplasmic reticulum, Feb. 2006, Cytokine 33, pp. 264-273.

Weiss, A. et al, The Role of T3 Surface Molecules in the Activation of Human T cells: A Two-Stimulus Requirement for IL 2 Production Reflects Events Occurring at a Pre-translational level. Journal of Immunology, Jul. 1984, vol. 133, No. 1, pp. 123-128.

Wu, L. et al, A Novel Polyacetylene Significantly Inhibits Angiogenesis and Promotes Apoptosis in Human Endothelial Cells throught Activation of the CDK Inhibitors and Caspase-7, 2007, Planta Med, 73, pp. 665-661.

Wu, L. et al, Polyacetylenes Function as Anti-angiogenic Agents, Nov. 2004, Pharmaceutical Research, vol. 21, No. 11, pp. 2112-2119.

WB : Avidin   CB staining

B

| Band | Protein name | Protein ID | MW (kDa) | Mascot score | Sequence Coverage (%) | No. of unique matched peptides |
|---|---|---|---|---|---|---|
| 1 | Pdia4 | NP_004902 | 72.9 | 1267 | 40 | 28 |
| 1 | Hspa5 | NP_005338 | 72.3 | 687 | 30 | 18 |

PDIA4, TARGET OF CYTOPILOYNE DERIVATIVES, FOR TUMOR DIAGNOSIS AND TREATMENT

RELATED APPLICATIONS

The present application claims priority under 35 U.S.C. §119(e) to U.S. Provisional Application No. 61/333,060, filed on May 10, 2010, which is herein expressly incorporated by reference.

REFERENCE TO SEQUENCE LISTING, TABLE

The present application is being filed along with a Sequence Listing in electronic format. The Sequence Listing is provided as a file entitled SEQLISTING.TXT, created May 9, 2011, which is 4 Kb in size. The information in the electronic format of the Sequence Listing is incorporated herein by reference in its entirety.

BACKGROUND

1. Field

The present application relates generally to the involvement of Pdia4 in cell growth and cell proliferation, and methods of diagnosing cancer associated with the presence and/or amount of Pdia4.

2. Description of the Related Art

Polyynes are a group of organic compounds with two or more carbon triple bonds. So far, over 1000 polyynes have been isolated from plants, fungi, bacteria and corals (Shi Shun, A. L., et al. (2006) *Angew. Chem. Int. Ed. Engl.* 45(7), 1034-1057). Polyynic compounds have a variety of biological activities. Many of them have been shown to have a broad range of medicinal and biological properties such as anti-tumor, anti-inflammation, anti-angiogenetic, anti-diabetic, anti-microbial, anti-viral, anti-protozan, and phototoxic activities (Shi Shun, A. L., et al. (2006) *Angew. Chem. Int. Ed. Engl.* 45(7), 1034-1057; Dembitsky, V. M. (2006)*Lipids* 41(10), 883-924). More than 300 polyynes have been reported to show cytotoxic activity against a variety of tumor cells (Dembitsky, V. M. (2006)*Lipids* 41(10), 883-924). However, their anti-tumor mechanism is poorly studied.

Two linear chain polyynes of *Bidens pilosa*, cytopiloyne (CP) and its aglycone (CPA), inhibit T cell proliferation and induce apoptosis of umbilical vein endothelium cells. CP and CPA belong to a subclass of polyynes with a linear chain structure of four conjugated triple bonds (Wu, L. W., et al. (2004)*Pharm. Res.* 21(11), 2112-2119; Chiang, Y. M., et al. (2007) *J. Ethnopharmacol.* 110(3), 532-538). Both compounds were initially identified from *Bidens pilosa* plant with a cytotoxic activity against leukemia and carcinoma (Sundararajan, P., et al. (2006)*Afr. Health Sci.* 6(1), 27-30; Chang, J. S., et al. (2001)*Am. J. Ch. Med.* 29(2), 303-312). CP inhibits T-cell proliferation (Chang, C. L., et al. (2007) *J. Immunol.* 178(11), 6984-6993), and CPA promotes apoptosis of endothelial cells and in turn, angiogenesis, via disruption of cell cycle (Wu, L. W., et al. (2004)*Pharm. Res.* 21(11), 2112-2119; Wu, L. W., et al. (2007)*Planta Med.* 73(7), 655-661). But anti-tumor effect and mechanism of CP derivatives are poorly understood.

Protein disulfide isomerases (PDIs) constitute a family of enzymes which catalyze oxidation and reduction of disulfide bonds during the formation of newly synthesized proteins and help protein folding. PDIs also act as chaperone and most of the PDIs are located in the lumen of the endoplasmic reticulum (ER), but some PDIs are located on other cellular compartments. The family of PDIs play role in mammalian development and diseases (Ni, M., et al. (2007) *FEBS letters* 581 (19), 3641-3651). They possess endoreticulum (ER) functions, e.g., formation and exchange of disulfide bonds during protein synthesis and folding. Besides, they have non-ER functions probably via conformational maintenance of specific proteins, which are implicated in pathogen infection (Ou, W., et al. (2006)*Virology* 350(2), 406-417; Naguleswaran, A., et al. (2005) *Int. J. Parasitol.* 35(13), 1459-1472), fertilization (Ellerman, D. A., et al. (2006)*Developmental cell* 10(6), 831-837), coagulation (Manukyan, D., et al. (2008) *Thrombosis research* 122 Suppl 1, S19-22), immunity (Garbi, N., et al. (2006)*Nat Immunol* 7(1), 93-102), tumor metastasis (Goplen, D., et al. (2006)*Cancer research* 66(20), 9895-9902) or cell viability/growth (Li, X. A., et al. (1991) *Molecular and cellular biology* 11(7), 3446-3453; Severino, A., et al. (2007) *J Am Coll Cardiol* 50(11), 1029-1037; U.S. Pat. Pub. No. 2003/0152565). PCT publication WO2010/004214 relates to a method for the in vitro diagnosis of colorectal cancer by determining the presence of the protein disulfide isomerase tumor marker through the use of at least one anti-PDI monoclonal antibody against a PDI epitope. Cellular localization of some PDIs was found in cytosol (ER) and unusual compartments (cell surface, nucleus, etc.). This localization might be related to the ER and non-ER functions (Turano, C., et al. (2002)*Journal of cellular physiology* 193 (2), 154-163. The role of PDIs in cell growth is poorly studied, not to mention the mechanism by which PDIs regulate cell growth. Probably, yeast study comes to the clearest conclusion indicating that PDIs are essential for cell viability (Farquhar, R., et al. (1991) *Gene* 108(1), 81-89) and the function of all 5 yeast PDIs may not be interchangeable (Norgaard, P., et al. (2001) *J. Cell Biol.* 152(3), 553-562). Consistently, a general PDI inhibitor, bacitricin, was shown to cause tumor cell death (Lovat, P. E., et al. (2008)*Cancer Res.* 68(13), 5363-5369). However, mice deficient in Pdia3 were shown to be lethal at embryonic stage (Garbi, N., et al. (2006) *Nat Immunol* 7(1), 93-102), suggesting that some PDIs may be functionally not redundant.

In mammals, the 9 PDI members are involved in a broad range of cell functions. There are 9 PDI members containing 1 to 3 CGHC active sites in human. The PDIs have been proposed to have different redox potentials, which act sequentially on nascent protein, or distinct substrate specificity in the protein folding process (Maattanen, P., et al. (2006) *Biochem Cell Biol* 84(6), 881-889). Among the 9 human PDIs, Pdia-4 is the only PDI member with 3 CGHC motifs (Maattanen, P., et al. (2006)*Biochem Cell Biol* 84(6), 881-889). Pdia4 was reported to be implicated in the unfolded protein response in the ER and acts as chaperone of calcium-binding properties. Up-regulation of Pdia4 was found in highly metastatistic HCC cell lines. In addition, up-regulation of Pdia4 also occurs when DG44 cells were treated with ionophore which causes ER stress. Little is known about the biological role of Pdia4. The expression of Pdia4 whose promoter contains ER stress responsive element could be induced by ER stress (Parker, R., et al. (2001)*Molecular and cellular biology* 21(9), 3220-3233; Li, X. A., et al. (1991) *Molecular and cellular biology* 11(7), 3446-3453). Pdia4 and other ER proteins such as Hspa5, Hsp90β1, Pdi, Calr, and Cabp 1 were found to associate with different nascent proteins in ER (Kuznetsov, G., Chen, L. B., and Nigam, S. K. (1994) *The Journal of biological chemistry* 269(37), 22990-22995; Feng, W., et al. (1995) *The Journal of biological chemistry* 270(20), 11851-11859; Vandenbroeck, K., et al. (2006) *Cytokine* 33(5), 264-273). Pdia4 appeared to complex with Hspa5 as well as Hsp90β1. Expression decrease of Pdia4, Hspa5 and Hsp90β1 by the amplification of ER stress responsive element in CHO cells decrease cell growth and viability (Li, X. A., et al. (1991) *Molecular and cellular biology* 11(7), 3446-3453). Despite a possible link between Pdia4 and cell growth and viability, little is known about the gene function of Pdia-4 in cell growth and viability.

Acute lymphocytic leukemia (ALL) is the most common cancer of childhood. Its incidence rate was 1.6 per 100,000 men and women per year in United States. Around 15% of acute lymphocytic leukemia cases are T cell acute lymphocytic leukemia (T-ALL), a disease caused by malignant transformation of T cells (Grabher, C., et al. (2006)*Nat. Rev. Cancer* 6(5), 347-359). T-ALL pathogenesis is related to genetic alterations or aberrant expression of oncogenes or tumor suppressor genes. Though treatment outcomes for T-ALL have been much improved, novel lead compounds for T-ALL are necessary. Jurkat cells, which were established from a patient with T cell acute lymphocytic leukemia, are a physiologically relevant tumor model of T-ALL (Gillis, S., et al. (1980) *J. Exp. Med.* 152(6), 1709-1719).

In chemical biology, small-molecule compounds are used as tools to explore the impact and mechanism of biology (Spring, D. R. (2005) *Chem. Soc. Rev.* 34(6), 472-482). The key step to chemical biology study is target identification of the compounds, which is the hardest task, too. This identification helps discover new druggable genes, expand the signaling network and understand the action of compounds (Burdine, L., et al. (2004) *Chem. Biol.* 11(5). 593-597).

There is a need in the art to determine the molecular targets of CP and CPA in vivo and the likely mechanism of the polyynes for the production of screening methods and research tools.

SUMMARY OF THE INVENTION

Some embodiments disclosed herein include a method of diagnosing cancer, the method comprising (a) performing an assay using a biological sample from a subject to determine the presence and/or amount of Pdia4; and (b) diagnosing the subject with cancer if the results from the determination indicates a presence and/or amount Pdia4 associated with the cancer.

Additional embodiments disclosed herein include a method for identifying tumors likely to respond to treatment with a Pdia4 antagonist comprising a) administering a Pdia4 antagonist to a subject having a tumor and b) monitoring an indicator of microvessel maturation in the tumor over a period time after administration of the Pdia4 antagonist; wherein a decrease in the microvessel density of the tumor in response to the Pdia4 antagonist administration is indicative of the tumor being responsive to the subsequent a Pdia4 antagonist.

These methods may also comprise administering to the subject with a Pdia4 antagonist.

In some embodiments, the methods further comprise administering one or more second chemotherapeutic agents to the subject. In some embodiments, the second chemotherapeutic agent is the same as the Pdia4 antagonist. In other embodiments, the second chemotherapeutic agent is different from the Pdia4 antagonist.

In some embodiments, the Pdia4 antagonist inhibits expression of Pdia4 protein. In other embodiments, the Pdia4 antagonist inhibits the biological activity of Pdia4. In yet other embodiments, the Pdia4 antagonist inactivates the Pdia4 gene or its promoter. In some embodiments, the Pdia4 antagonist is selected from the group consisting of an antisense molecule, a triple helix molecule, a ribozyme and an siRNA. In some embodiments, the siRNA comprises SEQ ID NO: 1, SEQ ID NO:2, or SEQ ID NO:3. In some embodiments, the Pdia4 antagonist is selected from the group consisting of an antibody to Pdia4, polyynes and bacitricin. In some embodiments, the Pdia4 antagonist is a combination of a taxane and doxirubicin. The taxane can be paclitaxel or docetaxel.

In some embodiments, the methods further comprise administering radiation therapy to the subject. In some embodiments, the second chemotherapeutic agent is selected from the group consisting of etoposide, CPT-I1 and temozolomide. In other embodiments, the second chemotherapeutic agent is selected from the group consisting of CPT-I 1, temozolomide (TMZ), bleomycin, carboplatin, chlorambucil, cisplatin, colchicine, cyclophosphamide, daunorubicin, dactinomycin, diethylstilbestrol doxorubicin, etoposide, 5-fluorouracil, floxuridine, melphalan, methotrexate, mitomycin, 6-mercaptopurine, teniposide, 6-thioguanine, vincristine and vinblastine.

In some embodiments, the cancer is a glioblastoma. In some embodiments, the Pdia4 antagonist is not kringle5 or a derivative of kringle 5.

In some embodiments, the Pdia4 antagonist inhibits expression of Pdia4 protein. The Pdia4 antagonist can inhibit biological activity of Pdia4, or inactivate Pdia4 gene or its promoter. In some embodiments, the Pdia4 antagonist is selected from the group consisting of an antisense molecule, a triple helix molecule, a ribozyme and an siRNA.

BRIEF DESCRIPTION OF THE DRAWINGS

FIGS. 1A-C Effect of cytopiloyne (CP) and cytopiloyne aglycone (CPA) on cell growth, death and proliferation. FIG. 1A-B are graphs showing effects of CP and CPA on growth and death of Jurkat cells. Jurkat cells were grown in RPMI medium in the presence of DMSO (−), CP and CPA at the indicated concentrations for 6 days. Numbers of living cells (FIG. 1A) and dead cells (FIG. 1B) were counted by using eosin Y and hematocytometer. Growth (%) is defined as 100% multiplied by the ratio of the living cell number with compound treatment to that with the control treatment. Death (%) is defined as 100% multiplied by the ratio of the dead cell number to a total of cells (both living and dead). FIG. 1C is a graph showing effect of CP and CPA on proliferation of Jurkat cells. Jurkat cells, which were already labeled with AFSE, were grown under the same condition as the Jurkat cells shown in FIGS. 1A-B. Mean fluorescent intensity (MFI) of the cells on days 0, 2, 4 and 6 were determined using FACS.

FIG. 2A shows identification of BCP-bound protein. Biotinylated CP (BCP) is a conjugate of biotin and CP. Jurkat cells were incubated with DMSO (lane 1) or BCP (lane 2). Fifty μg of total lysates underwent Western blot with avidin-POD (FIG. 2A left panel). The rest of total lysates was precipitated with streptavidin-agarose beads, and the precipitates were separated, followed by coomassie blue staining (CB) (FIG. 2A right panel). The BCP-bound proteins were shown in Band 1. FIG. 2B shows identification of BCP-bound proteins (band 1) by MS. Band 1 was cut and underwent in gel digestion, followed by LC/QTOF analysis. The identity of two proteins, Pdia4 and Hspa5, is indicated. FIG. 2C shows interaction of endogenous Pdia4 and Hspa5. Jurkat cells were incubated with DSP. Total lysate (lane 1) or the precipitates with anti-Pdia4 antibody plus streptavidin bead (lane 2) or with streptavidin bead (lane 3) underwent Western blot with ant-Hspa5 or ant-Pdia4 antibody.

FIG. 3A-E show target validation of CP derivatives. FIG. 3A is a western blot showing the binding of GST fusion proteins to BCP. Bead-bound GST-TecSH3 (lanes 1-2), GST- Hspa5 (lanes 3-4) or GST-Pdia4 (lanes 5-6) proteins were incubated with DMSO vehicle (lanes 1, 3 and 5) or BCP (lanes 2, 4 and 6). After pulled down, the proteins underwent Western blot with avidin-POD. FIG. 3B shows competition assays for the binding of GST-Pdia4 and CP derivatives. GST-Pdia4 was incubated with DMSO (lane 1) or BCP (lanes 2-6) in the presence of CP (10× and 50×) or CPA (10× and 50×) for overnight. The proteins were analyzed as (A). FIG. 3C shows interference of GST-Pdia4/BCP interaction by reducing agent. GST-Pdia4 was incubated with DMSO (lanes 1 and 3), BCP (lane 2) or BCP plus 2-mercaptoethanol (ME) (lane 4) for overnight. The proteins were analyzed as (A). FIG. 3D shows in vivo interaction of Pdia4 with BCP. Jurkat cells were incubated with DMSO (lanes 1 and 3) or BCP (lanes 2 and 4). Total lysates underwent Western blot with anti-Pdia4 antibody. FIG. 3E shows MS/MS analysis of GST-Pdia4 CPA adduct. GST-Pdia4 was incubated with CPA. After trypsin digestion, the peptides underwent LC/MS/MS analysis. Sequence of the CPA-modified peptide corresponding to residues 185-210 is indicated. FIG. 3F shows inhibition of the disulfide isomerase activity of GST-Pdia4 by CPA. Reduced BPTI was incubated with redox buffer in the presence of vehicle, GST, GST-Pdia4 or GST-Pdia4 with CPA. Enzymatic activity is represented as fraction remaining (%) of the reduced BPTI.

FIGS. 4A-F show a functional study of Pdia4. FIG. 4A shows a confocal analysis of Pdia4 localization. Jurkat cells were stained with non-immunized rabbit serum plus FITC-conjugated second antibody (CTR), anti-Pdia4 antibody plus FITC-conjugated second antibody (anti-Pdia4) and BCP and avidin-FITC (BCP), followed by DAPI double staining. FIG. 4B shows cellular distribution of Pdia4 in primary $CD4^+$ T cells and Jurkat cells. Cytoplasmic (C), nuclear (N) and membrane (M) proteins of human $CD4^+$ T cells (pT, $0.5 \times 10^6$) and Jurkat cells E6.1 ($0.5 \times 10^6$) were analyzed using Western blot. FIG. 4C shows the effect of Pdia4 knockdown on cell growth. Jurkat cells were infected with lentiviral vector pPGK-GFP (Mock) or pLKO.1-D9-GFP (A4 KD). The cells were grown in RPMI supplemented with 10% or 2.5% FBS for 6 days. Cell number of the 2 clones was counted. Pdia4 expression level of the 2 clones was determined using Western blot with anti-Pdia4 and anti-Tubulin antibodies. FIG. 4D shows the effect of Pdia4 knockdown on cell proliferation. The same cells from (FIG. 4C) were stained with AFSE and grown in RPMI/10% FBS were grown for 6 days. AFSE intensity of the cells was determined using FACS. FIG. 4E shows the effect of Pdia4 knockdown on caspase 3/7 activity. Total lysates of the cells (A) were incubated with fluorescent caspase 3/7 substrate. The caspase 3/7 activity in RLU was measured. FIG. 4F shows the additive effect of Pdia4 and Hspa5 on cell growth. Jurkat cells infected with lentiviral vector pPGK-GFP (Mock), pLKO.1-D9-GFP (A4 KD), pLKO.1-B2-Hyg (A5 KD) or pLKO.1-D9-GFP (KD)/pLKO.1-B2-Hyg (A4/A5 KD).

DETAILED DESCRIPTION

Disclosed herein are methods of diagnosing cancer associated with the presence and/or amount of Pdia4 in a biological sample. It was determined that two linear chain polyynes, CP and CPA, inhibited cell growth of Jurkat cells, a T-ALL line, via inhibition of proliferation and/or promotion of cell death; and a protein disulfide isomerase, Pdia4, is the main target of CP derivatives. It was also determined that expression of Pdia4 was up-regulated in tumor cells such as leukemia, breast cancer cells and kidney fibroblast tumors; and that Pdia4 promotes tumor cell growth via regulation of proliferation and apoptosis, as evidenced by leukemia Jurkat cells. Thus, the presence and/or amount of Pdia4 in a sample are indicative of cancer. These discoveries enable development of methods for the diagnosis of cancer.

Definition

As used herein, the term "cancer" refers to animal cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus.

In some embodiments, the cancer can be leukemia. For example, the cancer can be acute leukemia, including, but not limited to, acute lymphocytic leukemia (ALL), acute myeloid leukemia (AML) and acute monocytic leukemia. In other embodiments, the cancer can be breast cancer. In some other embodiments, the cancer can be kidney fibroblast tumor.

In some embodiments, the cancer can be a carcinoma. The term "carcinoma" is art recognized and refers to malignancies of epithelial or endocrine tissues. The term includes carcinosarcomas, which include malignant tumors composed of carcinomatous and sarcomatous tissues. Examples of carcinomas include, but are not limited to, esophageal carcinoma; hepatocellular carcinoma; basal cell carcinoma, squamous cell carcinoma (various tissues); bladder carcinoma, including transitional cell carcinoma; bronchogenic carcinoma; colon carcinoma; colorectal carcinoma; gastric carcinoma; lung carcinoma, including small cell carcinoma and non-small cell carcinoma of the lung; adrenocortical carcinoma; thyroid carcinoma; pancreatic carcinoma; breast carcinoma; ovarian carcinoma; prostate carcinoma; adenocarcinoma; sweat gland carcinoma; sebaceous gland carcinoma; papillary carcinoma; papillary adenocarcinoma; cystadenocarcinoma; medullary carcinoma; renal cell carcinoma; ductal carcinoma in situ or bile duct carcinoma; choriocarcinoma; seminoma; embryonal carcinoma; Wilm's tumor; cervical carcinoma; uterine carcinoma; testicular carcinoma; osteogenic carcinoma; epithelieal carcinoma; nasopharyngeal carcinoma; etc.

In other embodiments, the cancer can be a sarcoma. Examples of sarcomas include, but are not limited to, fibrosarcoma, myxosarcoma, liposarcoma, chondrosarcoma, chordoma, osteogenic sarcoma, osteosarcoma, angio sarcoma, endothelio sarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

In still other embodiments, the cancer can be a tumor, such as a solid tumor. Examples of solid tumors include, but are not limited to, glioblastoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Examples of leukemias include, but are not limited to, chronic myeloproliferative syndromes; acute myelogenous leukemias; chronic lymphocytic leukemias, including B-cell CLL, T-cell CLL prolymphocytic leukemia, and hairy cell leukemia; and acute lymphoblastic leukemias.

In yet other embodiments, the cancer can be lymphoma. Examples of lymphomas include, but are not limited to, B-cell lymphomas, such as Burkitt's lymphoma; Hodgkin's lymphoma; and the like.

As used herein, the term "antagonist" is used in the broadest sense and refers to any molecule or compound that partially or fully blocks, inhibits or neutralizes a biological activity mediated by Pdia4, for example by preventing or reducing the activation of Pdia4 or the enzymatic activity (e.g., protein disulfide isomerase activity) of Pdia4. The term "Pdia4 antagonist" also includes any molecule that mimics a biological activity mediated by Pdia4 and specifically changes, preferably abolishes or reduces the function or expression of Pdia4, prevents or reduces the binding the Pdia4 with its binding partners (e.g., CP and CPA) or substrates, or abolishes or reduces the efficiency of isomerase activity. In some embodiments, the inhibition of activity is at least 5%, for example, at least any of the following: 5, 10, 15, 20, 25, 30, 35, 40, 45, 50, 55, 60, 65, 70, 75, 80, 85, 90, 91, 92, 93, 94, 95, 96, 97, 98, 99 percent or greater inhibition, including any range above any of the previous values and any range defined between any of the two previous values. Antagonists can include, but are not limited to, small organic and inorganic molecules, nucleic acids, peptides, peptide mimetics and neutralizing antibodies.

As used herein, the term "chemotherapeutic agent" refers to any therapeutic agent that can be used for treating or ameliorating a cell proliferative disorder such as tumors or cancer. Examples of chemotherapeutic agents include but are not limited to an antineoplastic agent, an alkylating agent, a plant alkaloid, an antimicrobial agent, a sulfonamide, an antiviral agent, a platinum agent, and other anticancer agents known in the art. Specific examples of chemotherapeutic agents include, but are not limited to, cisplatin, carboplatin, busulphan, methotrexate, daunorubicin, doxorubicin, cyclophosphamide, mephalan, vincristine, vinblastine, chlorambucil, paclitaxel, gemcitabine, and others known in the art. (See, e.g., Goodman & Gilman's, The Pharmacological Basis of Therapeutics (9th Ed) (Goodman, et al., eds.) (McGraw-Hill) (1996); and 1999 Physician's Desk Reference (1998)). In some embodiments, a chemotherapeutic agent can be CPT-I 1, temozolomide (TMZ), bleomycin, carboplatin, chlorambucil, cisplatin, colchicine, cyclophosphamide, daunorubicin, dactinomycin, diethylstilbestrol doxorubicin, etoposide, 5-fluorouracil, floxuridine, melphalan, methotrexate, mitomycin, 6-mercaptopurine, teniposide, 6-thioguanine, vincristine, vinblastine, and a combination thereof.

As used herein, the term "promoter" refers to an untranslated DNA sequence usually located upstream of the coding region that contains the binding site for RNA polymerase II and initiates transcription of the DNA. The promoter region can also include other elements that act as regulators of gene expression.

As used herein, the term "expression" refers to the transcription and/or translation of an endogenous gene, transgene or coding region in a cell. In the case of an antisense construct, expression may refer to the transcription of the antisense DNA only.

As used herein, the term "antibody" is used herein in the broadest sense and specifically covers human, non-human (e.g., murine) and humanized antibodies, including, but not limited to, full-length monoclonal antibodies, polyclonal antibodies, multi-specific antibodies, and antibody fragments, including intrabodies, so long as they exhibit a desired biological activity. In general, an antibody exhibits binding specificity to a specific antigen. The term "antibody" is meant to include intact immunoglobulin or antibody molecules as well as fragments thereof, such as Fa, F (ab')$_2$, and Fv, which are capable of binding an antigenic determinant.

As used herein, the term "biological property" or "biological activity" refers to a biological function caused by a protein, such as Pdia4 or other compound disclosed herein. For example, biological properties of Pdia4 include, but are not limited to, regulation of cell growth, cell proliferation, and cell cycle, promoting tumor cell growth (e.g., via regulation of proliferation and apoptosis) and modulating of cell death. With regards to Pdia4 antagonists (or inhibitors of Pdia4), biological activity refers, in part, to the ability to fully or partially abolish, eliminate, reduce, or decrease the biological properties of Pdia4. Preferred biologic activities of antagonists of Pdia4 include, but are not limited to, treatment, alleviation, prevention of cancer.

As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

As used herein, the term "subject" refers to a mammal, e.g., a human, or to an experimental or animal or disease model. The subject can also be a non-human animal, e.g., a horse, cow, goat, or other domestic animal.

Pdia4

Figure 1:
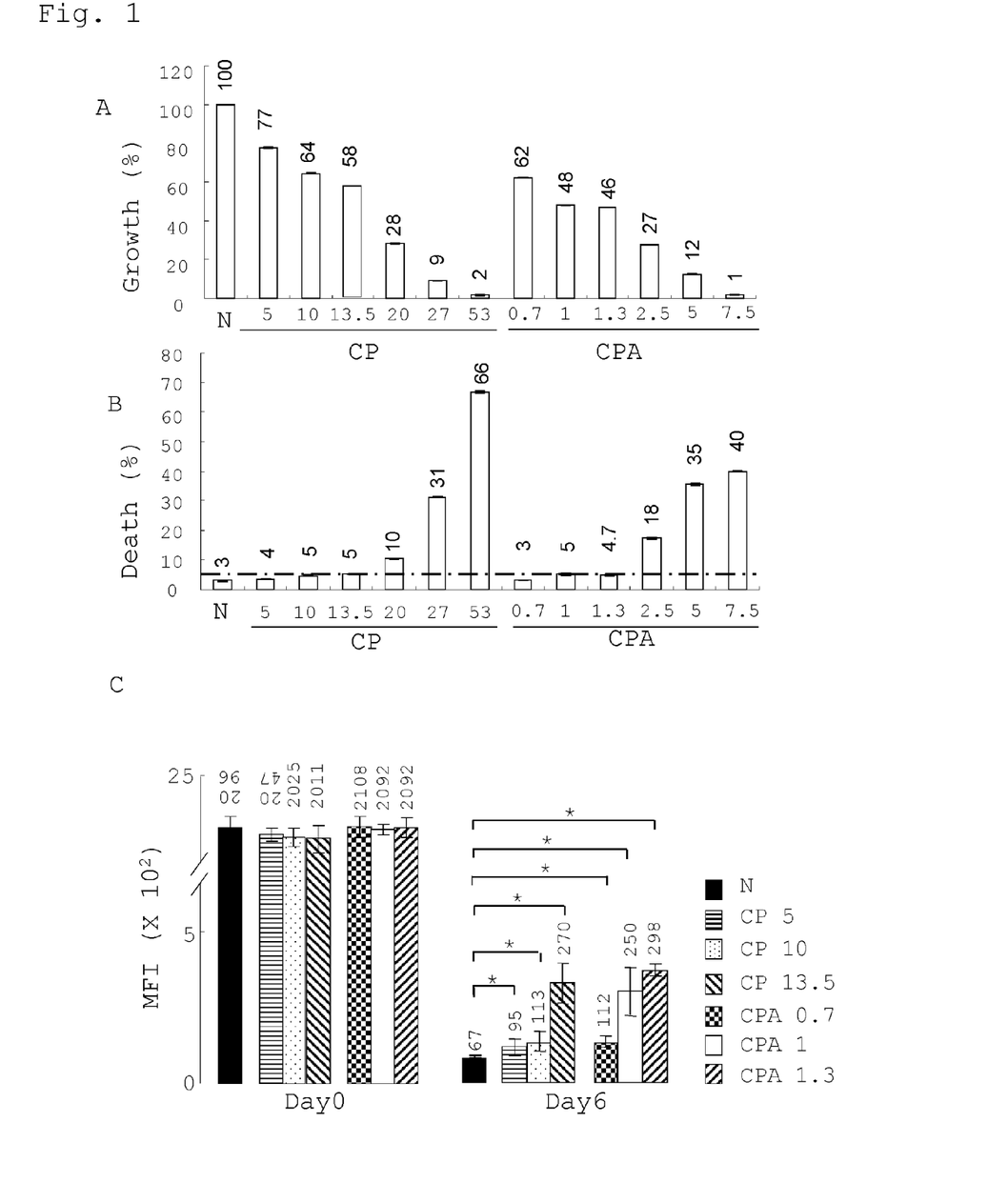
Figure 4:
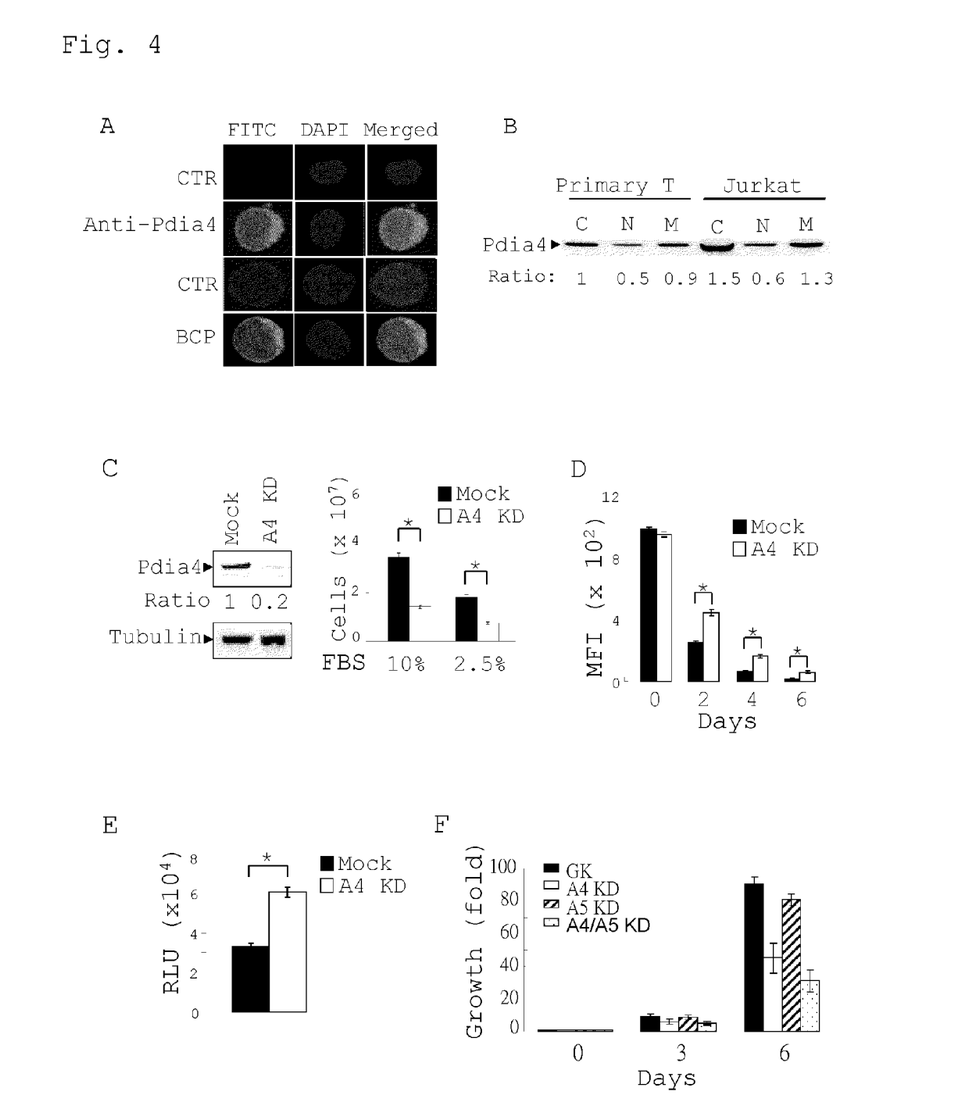

As disclosed herein, the family of protein disulfide isomerases (PDIs) is invovled in regulation of tumor growth and/or metastasis. For instance, a PDI was overexpressed in invasive tumor cells (Goplen, D., et al. (2006)*Cancer research* 66(20), 9895-9902). Inhibition of PDIs by bacitricin caused tumor death (Lovat, P. E., et al. (2008) *Cancer research* 68(13), 5363-5369). The present application discloses the role of Pdia4 in tumor growth/metastasis. For example, as disclosed below, Pdia4 is up-regulated in several types of tumor (FIG. 4), and CP derivatives were effective inhibitors of cell growth of Jurkat cells via inhibition of the disulfide isomerase activity of Pdia4 (FIG. 1). Furthermore, Pida4 knockdown had similar effects on Jurkat cell growth as the treatment of CP derivatives (FIG. 4). Also, precious publications showed that CP inhibited T cell proliferation (Chang, C. L., et al. (2007) *J Immunol.* 178(11), 6984-6993) and CPA induced cell death of umbilical vein endothelial cells (Wu, L. W., et al. (2004)*Pharm. Res.* 21(11), 2112-2119; Wu, L. W., et al. (2007) *Planta Med.* 73(7), 655-661).

PDIs are also essential for cell growth and survival (Farquhar, R., et al. (1991) *Gene* 108(1), 81-89). In mammalians, 9 PDIs possess 1 to 3 CGHC motifs. The only available data on PDI family are that ablation of Pdia3 in mice dampens embryonic development and WIC/peptide assembly (Garbi, N., et al. (2006)*Nat Immunol* 7(1), 93-102). However, little is known about the function of other PDIs, such as Pdia4. Pdia4 is characterized by several unique features, including the only PDI with the highest number (three) of CGHC motifs, inducible expression by tumors and ER stress, the absence of known functional redundancy and disulfide isomerase/chaperone activity for specific substrates. As disclosed below, inactivation or knockdown of Pdia4 (FIG. 1 and FIG. 4) inhibits cell growth and proliferation, and increases cell death.

Figure 2:
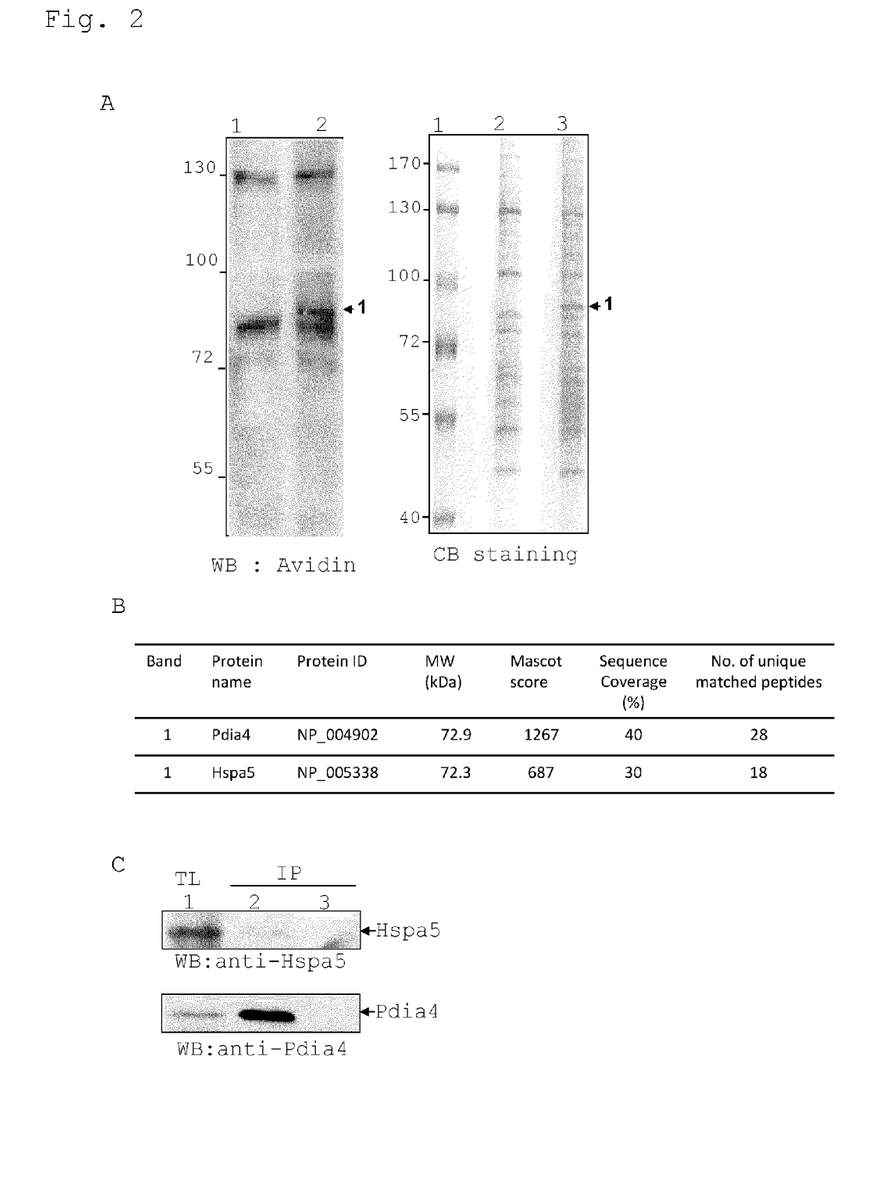

Cysteine acts as an active site for PDIs and other enzymes. Modification of cysteine has been shown to damage catalytic activity of Pdi (Carbone, D. L., (2005)*Chem. Res. Toxicol.* 18(8), 1324-1331). MS data on CPA/Pdia4 adduct showed that CPA only bound to the second active motif of Pdia4 via cysteine residues in a covalent fashion (FIG. 2). This adduct indeed inhibited the isomerase activity of Pdia4 (FIG. 2). The data are in good agreement with the publication describing that mutation on the second CGHC motif largely compromised substrate binding and catalytic activity of Pdia4 (Satoh, M., et al. (2005)*Cell Stress Chap.* 10(3), 211-220). Besides, our data support the explanation that CPA has easy access to the 2nd CGHC motif of Pdia4. However, we could not detect any CPA in the first and third CGHC sites. Another big issue is that BCP had a preferential binding affinity for Pdia4, but not the other PDIs, in Jurkat cells. There are several possible reasons for this. One is that Pdia4 is the most abundant PDIs in Jurkat cells. Second, each PDI may have its specific substrates (Maattanen, P., et al. (2006)*Biochem Cell Biol* 84(6), 881-889). Third, PDI family is thought to be not functionally redundant (Norgaard, P., et al. (2001) *J Cell Biol* 152(3), 553-562).

Pdia4 Antagonists

As discussed above, the term "antagonist" is used in the broadest sense and refers to any molecule or compound that partially or fully blocks, inhibits or neutralizes a biological activity mediated by Pdia4, for example by preventing or reducing the activation of Pdia4 or the enzymatic activity (e.g., protein disulfide isomerase activity) of Pdia4. The term "Pdia4 antagonist" also includes any molecule that mimics a biological activity mediated by Pdia4 and specifically changes, preferably abolishes or reduces the function or expression of Pdia4, prevents or reduces the binding the Pdia4 with its binding partners (e.g., CP and CPA) or substrates, or abolishes or reduces the efficiency of isomerase activity.

The method by which Pdia4 is antagonized is not limited in any way. In some embodiments, the Pdia4 antagonist can act directly on Pdia4, for example by binding to Pdia4, to prevent or reduce activation of Pdia4. In some embodiments, the Pdia4 antagonist can interfere, preferably abolish or reduce, Pdia4 from interacting with a binding partner or a substrate, such as Hspa5. In some embodiments, the Pdia4 antagonist can modulate the level of Pdia4 gene expression, for example, inhibiting or reducing the transcription of Pdia4 gene. In some embodiments, the Pdia4 antagonist can modulate the level of Pdia4 protein in cells by, for example, inhibiting or reducing the translation of Pdia4 mRNA, or increasing the degradation of Pdia4 mRNA or Pdia4 protein.

The types of Pdia4 antagonists are not limited in anyway. Pdia4 antagonists include, for example, small molecules, nucleic acids, antibodies, peptides, etc. In one embodiment, the Pdia4 antagonist can be a small molecule that binds to Pdia4. In some embodiments, the Pdia4 antagonist can be a compound that blocks interaction of Pdia4 and it binding partner. In some embodiments, the Pdia4 antagonist is a compound that blocks Pdia4 activation. In some embodiments, the Pdia4 antagonist inhibits expression of Pdia4 protein. In other embodiments, the Pdia4 antagonist inhibits the biological activity of Pdia4. In yet other embodiments, the Pdia4 antagonist inactivates the Pdia4 gene or its promoter. In some embodiments, the Pdia4 antagonist is selected from the group consisting of an antisense molecule, a triple helix molecule, a ribozyme and an siRNA. In some embodiments, the Pdia4 antagonist is a nucleic acid, for example, an anti-Pdia4 small-hairpin RNA (shRNA) or a Pdia4 anti-sense RNA (siRNA). In some embodiments, the siRNA comprises SEQ ID NO: 1 (CCGGGCUUGU GUUGACCAAA GAGAACUCGA GUUCUCUUUG GUCAACACAA GCUUUUUG), SEQ ID NO:2 (CCGGCCAAGA AGUACAAGGG CCAAACUCGA GUUUGGCCCU UGUACUUCUU GGUUUUUG), or SEQ ID NO:3 (CCGGGCAAGG UGUCAAACGA UGCUACUCGA GUAGCAUCGU UUGACACCUU GCU- UUUUG). In some embodiments, the siRNA is generated in vivo from a plasmid encoding the DNA that has sequence corresponding to the siRNA sequence. In some embodiments, the corresponding DNA sequence can be SEQ ID NO: 4 (CCGGGCTTGTGTTGACCAAAGAGAACTC-GAGTTCTCTTTGGTCAACACAAGCTTT TTG, corresponds to SEQ ID NO: 1), SEQ ID NO: 5 (CCGGCCAA-GAAGTACAAGGGCCAAACTCGAGTTTGGCCCTTG-TACTTCTTGGTTT TTG; corresponds to SEQ ID NO:2), or SEQ ID NO: 6 (CCGGGCAAGGTGTCAAACGATGC-TACTCGAGTAGCATCGTTTGACACCTTGCTT TTTG, corresponds to SEQ ID NO: 3). In some embodiments, the Pdia4 antagonist is selected from the group consisting of an antibody to Pdia4, polyynes and bacitricin. In some embodiments, the Pdia4 antagonist is a combination of a taxane and doxirubicin. The taxane can be paclitaxel or docetaxel.

Antibodies that can block activation of Pdia4 are also suitable for use in methods disclosed herein. For example, an antibody can bind to Pdia4 and prevent interaction between Pdia4 and its binding partner and/or its substrate. In some embodiments, an antibody can also bind to one or more binding partner and/or substrate of Pdia4. The antibodies are not limited in any way, but are preferably monoclonal antibodies, more preferably human or humanized monoclonal antibodies. Antibodies to Pdia4 can be prepared using methods that are well known in the art and inhibitory antibodies can be identified using the methods described herein.

Predictive Medicine

Some aspects pertain to the field of predictive medicine in which diagnostic assays, prognostic assays, and monitoring clinical trials are used for prognostic (predictive) purposes to thereby treat an individual.

Methods of the invention can be used prenatally or to determine if a subject's offspring will be at risk for a disorder.

Diagnostic and Prognostic Assays

The presence, level, or absence of Pdia4 protein or nucleic acid in a biological sample can be evaluated by obtaining a biological sample from a test subject and contacting the biological sample with a compound or an agent capable of detecting Pdia4 protein or nucleic acid (e.g., mRNA, genomic DNA) that encodes Pdia4 protein such that the presence of Pdia4 protein or nucleic acid is detected in the biological sample. The term "biological sample" includes tissues, cells and biological fluids isolated from a subject, as well as tissues, cells and fluids present within a subject. An example of a biological sample is serum. The level of expression of the Pdia4 gene can be measured in a number of ways, including, but not limited to: measuring the mRNA encoded by the Pdia4 genes; measuring the amount of protein encoded by the Pdia4 genes; or measuring the activity of the protein encoded by the Pdia4 genes.

The level of mRNA corresponding to the Pdia4 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length Pdia4 nucleic acid, or a portion thereof.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the Pdia4 genes.

The level of mRNA in a sample that is encoded by one of Pdia4 can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self sustained sequence replication (Guatelli et al., (1990) Proc. Natl. Acad. Sci. USA 87:1874-1878), transcriptional amplification system (Kwoh et al., (1989), Proc. Natl. Acad. Sci. USA 86:1173-1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the Pdia4 gene being analyzed.

In another embodiment, the methods further contacting a control sample with a compound or agent capable of detecting Pdia4 mRNA, or genomic DNA, and comparing the presence of Pdia4 mRNA or genomic DNA in the control sample with the presence of Pdia4 mRNA or genomic DNA in the test sample.

A variety of methods can be used to determine the level of protein encoded by Pdia4. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect Pdia4 protein in a biological sample in vitro as well as in vivo. In vitro techniques for detection of Pdia4 protein include enzyme linked immunosorbent assays (ELISAs), immunoprecipitations, immunofluorescence, enzyme immunoassay (EIA), radioimmunoassay (MA), and Western blot analysis. In vivo techniques for detection of Pdia4 protein include introducing into a subject a labeled anti-Pdia4 antibody. For example, the antibody can be labeled with a radioactive marker whose presence and location in a subject can be detected by standard imaging techniques.

In another embodiment, the methods further include contacting the control sample with a compound or agent capable of detecting Pdia4 protein, and comparing the presence of Pdia4 protein in the control sample with the presence of Pdia4 protein in the test sample.

The invention also includes kits for detecting the presence of Pdia4 in a biological sample. For example, the kit can include a compound or agent capable of detecting Pdia4 protein or mRNA in a biological sample; and a standard. The compound or agent can be packaged in a suitable container. The kit can further comprise instructions for using the kit to detect Pdia4 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated Pdia4 expression or activity.

In one embodiment, a disease or disorder associated with aberrant or unwanted Pdia4 expression or activity is identified. A test sample is obtained from a subject and Pdia4 protein or nucleic acid (e.g., mRNA or genomic DNA) is evaluated, wherein the level, e.g., the presence or absence, of Pdia4 protein or nucleic acid is diagnostic for a subject having or at risk of developing a disease or disorder associated with aberrant or unwanted Pdia4 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted Pdia4 expression or activity.

Use of Pdia4 as Surrogate Marker

The Pdia4 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the Pdia4 molecules of the invention can be detected, and can be correlated with one or more biological states in vivo. For example, the Pdia4 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached. Examples of the use of surrogate markers in the art include: Koomen et al. (2000) J. Mass. Spectrorn. 35: 258-264; and James (1994) AIDS Treatment News Archive 209.

For example, microvessel density (MVD) is a surrogate marker which expressly reflects tumor angiogenesis and has been examined as a potential prognostic marker in numerous tumors. MRI technology provides a non-invasive approach for kinetic assessment of the effects of treatment on tumor associated microvessel density and function. MR imaging techniques, including dynamic contrast enhanced (DCE) MR imaging, apparent diffusion coefficient (ADC) mapping and blood oxygen level dependent (BOLD) functional MR (fMR), have been developed for non-invasive longitudinal characterization of tumor microvasculature and micro environmental parameters. The utility of MRI at 4.7 T for assessing intratumor vascular status with immunohistochemistry validation has been demonstrated (Bhattacharya et al., 2004, Clin Cancer Res., 10:8005-8017). MRI is a versatile technique that is used experimentally and clinically to characterize tumor microvasculature. Several parameters such as vascular volume, permeability, perfusion and oxygenation have been successfully assessed using MRI. Contrast-enhanced MRI is an extremely useful imaging technique that is extensively used in preclinical and clinical studies for the assessment of antivascular and antiangiogenic therapies. The ability to serially assess tumors by 4.7 T MR at various times during and after treatment could significantly aid in identifying tumor vasculature. The non-invasive nature of the technique combined with its multislice capabilities allows simultaneous visualization of tumor and normal tissues.

The Pdia4 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a Pdia4 marker) transcription or expression, the amplified marker can be in a quantity which is more readily detectable than the drug itself. Also, the marker can be more easily detected due to the nature of the marker itself; for example, using the methods described herein, anti-Pdia4 antibodies can be employed in an immune-based detection system for a Pdia4 protein marker, or Pdia4-specific radiolabeled probes can be used to detect a Pdia4 mRNA marker. Furthermore, the use of a pharmacodynamic marker can offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) Env. Health Perspect. 90: 229-238; Schentag (1999) Am. J. Health-Syst. Pharm. 56 Suppl. 3: S21-S24; and Nicolau (1999) Am. J. Health-Syst. Pharm. 56 Suppl. 3: S16-S20.

The Pdia4 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) Eur. J. Cancer 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., Pdia4 protein or RNA) for specific tumor markers in a subject, a drug or course of treatment can be selected that is optimized for the treatment of the specific tumor likely to be present in the subject. Similarly, the presence or absence of a specific sequence mutation in Pdia4 DNA can correlate with a Pdia4 drug response. The use of pharmacogenomic markers therefore permits the application of the most appropriate treatment for each subject without having to administer the therapy. In this paper, we first evaluated the effect of CP and CPA on cell growth of Jurkat cells, a leukemia T cell line. Next, we identified the molecular target(s) of the above polyynes and characterized the interaction between the target(s) and the polyynes. Finally, gene function of the target(s) in cell growth of Jurkat cells was investigated in vivo and in vivo.

EXAMPLES

The following examples, including the experiments conducted and results achieved are provided for illustrative purposes only and are not to be construed as limiting upon the present application.

Example 1

Preparation of Materials and Methods

Cells and Reagents

Jurkat E6.1 (Weiss, A., et al. (1984) *J. Immunol.* 133(1), 123-128), MCF-7, THP-1, HEK 293T cells were grown according to ATCC instructions. Human CD4+ T cells were grown in RPMI 1640 medium containing 10% fetal bovine serum (FBS) and nutrients as Jurkat cells (Chang, S. L., et al. (2007) *J. Ethnopharmacol.* 112(2), 232-236). Scid/beige mice were purchased from Charles River and housed according to the institutional guideline.

WST-1(4-[3-(4-Iodophenyl)-2-(4-nitrophenyl)-2H-5-trtrazolio]-1,3-benzenedisulfonate), 5-bromo-2-deoxyuridine (BrdU), propidine iodide (PI), protamine sulfate, puromycin dihydrochloride, β-mercaptoethanol, biotin, N-ethyl-N'-(3-dimethylaminopropyl)carbodiimide hydrochloride (EDCI), $Et_3N$, 1-hydroxybenzotriazole (HOBt), acetonitrile, ammonium bicarbonate, and iodoacetamide, were purchased from Sigma-Aldrich (St. Louis, Mo., USA). Trypsin was purchased from Promega (WI, USA). Caspase 3/7 fluorescent substrate and annexin V-PE was purchased from BioVision (CA, USA). Alexa Fluor 647 succinimidyl ester (AFSE), RPMI 1640, DMEM, FCS, penicillin/streptomycin/glutamate solution, and HEPES were purchased from Invitrogen (CA, USA). Bovine pancreatic trypsin inhibitor (BPTI, Trasylol®) was obtained from Bayer (Leverkusen, Germany). Anti-Hspa5, anti-GST, anti-Actin, anti-BrdU and anti-tubulin were purchased from Santa Cruz Biotechnology (Santa Cruz, Calif., USA). Anti-Pdia4 was obtained from Stressgen (MI, USA).

RNAi reagents were obtained from the TRC-Hs 1.0 library of National RNAi Core Facility (Academia Sinica, Taiwan).

Preparation of CPA, CP and BCP

CPA and CP were purified from *B. pilosa* as described in Wu, L. W., et al. (2004) *Pharm. Res.* 21(11), 2112-2119; and Chiang, Y. M., et al. (2007) *J. Ethnopharmacol.* 110(3), 532-538. For BCP synthesis, CP (24.1 mg) was incubated with a mixture of biotin (48.6 mg), EDCI (76.1 mg), HOBt (9.0 mg), and $Et_3N$ (55.9 μl) in DMF (2.15 ml) at room temperature for overnight. The reaction mixture was purified by semipreparative HPLC on a RP-18 column [Phenomenex Luna 5μ C18 (2), 250 mm×10 mm] using 40% MeCN in $H_2O$. BCP (4.7 mg) resulted from the conjugation of biotin with CP at 1-hydroxyl group of CP. Its NMR data was shown as follows. $^1$H NMR (500 MHz, $CDCl_3$): δ 1.46 (2H, p, J=7.5 Hz, $H_2$-6"), 1.58 (1H, m, $H_a$-5"), 1.67 (2H, p, J=7.5 Hz, $H_2$-7"), 1.73 (1H, m, $H_b$-5"), 1.84 (2H, td, J=7.0, 5.5 Hz, $H_2$-3), 1.98 (3H, s, $H_3$-13), 2.39 (2H, t, J=7.5 Hz, $H_2$-8"), 2.59 (2H, t, J=7.0 Hz, $H_2$-4), 2.71 (1H, d, J=12.5 Hz, $H_β$-3"), 2.93 (1H, dd, J=12.5, 5.0 Hz, $H_α$-3"), 3.16 (1H, dd, J=9.0, 8.0 Hz, H-2'), 3.20 (1H, dt, J=10.0, 5.0 Hz, H-4"), 3.27 (2H, m, H-4' and H-5'), 3.34 (1H, m, H-3'), 3.66 (1H, dd, J=11.5, 5.0 Hz, $H_a$-6'), 3.85 (1H, br d, J=11.5 Hz, $H_b$-6'), 3.94 (1H, p, J=5.5 Hz, H-2), 4.16 (1H, dd, J=11.0, 5.5 Hz, $H_a$-1), 4.30 (1H, m, $H_b$-1 and H-1"), 4.33 (1H, d, J=8.0 Hz, H-1'), and 4.49 (1H, dd, J=8.0, 5.0 Hz, H-2"). HR-ESI-MS m/z=611.2036 (calcd for $C_{29}H_{36}N_2O_9SNa$=611.2034). $^1$H NMR spectra were run on a Bruker Avance 500 AV spectrometer (500 MHz, $CD_3OD$). HR-ESI-MS was obtained on a Bruker BioTOF II mass spectrometer.

WST-1 Assay, Surface Staining and Intracellular Staining

WST-1 assays were performed to measure cell viability. Briefly, Jurkat cells (5×10$^3$) were grown in 100 μl per well. After 24 hour incubation with DMSO or CP derivatives, the cells were incubated with WST-1 at 37° C. for 30 minutes and characterized by 440 nm absorption. To stain BCP-bound proteins of Jurkat cells, 30 μM of DMSO, biotin and BCP was incubated with Jurkat cells for 24 hours, respectively. After washing, the cells underwent surface or intracellular staining with avidin-PE-TR (Caltag, Calif., USA), followed by fluorescence activated cell sorting (FACS) analysis. The FACS data were processed using FCS express 3.0 software (De Novo Inc, CA, USA).

Lentivirus Production and Infection pCMV-dR8.91, encoding Gag and Pol proteins, and pMD2G, encoding Env protein, are packaging vectors. pPGK-GFP, pLKO.1-D9 (TRCN0000049334) and PLKO.1-B (TRCN0000001023) contain an empty sequence, a Pdia4 RNAi sequence and a Hspa5 RNAi sequence in pLKO.1 lentiviral vector, respectively (Claffi, M., et al. (2006)*Gene* 366(2), 209-218). PLKO.1-D9-GFP was constructed by replacing the puromycin resistant gene of PLKO.1-D9 with a GFP cDNA. To produce lentiviral particles, HEK 293T cells were transfected with packaging plasmids and pPGK-GFP, pLKO.1-D9-GFP, PLKO.1-B or pLKO.1-D9-GFP/PLKO.1-B using TransIT-LT1 reagent (Mirus Bio, WI, USA). Lentiviral particles were collected 42 hour and 66 hour post-transfection and concentrated as described (Tiscornia, G., et al. (2006)*Nat. Protoc.* 1(1), 241-245). Lentiviral particles obtained from the transfection of pPGK-GFP, pLKO.1-D9-GFP, PLKO.1-B and pLKO.1-D9-GFP/PLKO.1-B were infected into stable clones of Jurkat cells, designated as GK, A4, A5 and A4/A5 cells, respectively.

Cell Growth, Cell Proliferation, Cell Cycle and Activity of Caspases 3/7

Jurkat cells were infected with different lentiviral particles 2 days prior to use. The cells were divided into 3 aliquots. One aliquot was tested for cell growth for 6 days and the number of live and dead cells was calculated using eosin Y. Another aliquot was stained with AFSE, monitored for cell proliferation for 6 days and followed byFACS analysis. Another aliquot was pulsed with 5-bromo-2-deoxyuridine (BrdU) for 30 minutes and chased for 0 to 48 hours. The cells underwent intracellular staining with anti-BrdU antibody and FACS analysis. The other aliquot was tested for caspase activity. Caspase 3/7 fluorescent substrate was incubated with 1 μg of total lysate and caspase activity, shown in relative light unit (RLU), was measured with Victor V luminescence counter. To evaluate in vivo tumor growth, lentivirally infected Jurkat cells (1×10$^6$) were subcutaneously inoculated into scid/beige mice. Tumor incidence, tumor size and survival rate of the tumor-bearing mice were scored.

Western Blot

To identify the BCP-bound protein, Jurkat cells (10$^7$) were incubated with DMSO or 200 μg BCP in 20 ml RPMI medium at for 37° C. 24 hours. After extensive washing, the cells were lyzed with 0.3 ml Brij lysis buffer. One part (50 μg) underwent western blot with peroxidase-conjugated avidin, followed by the development with an enhanced chemiluminescent kit. The rest of total lysates was precipitated by streptavidin agarose bead and underwent sodium dodecyl sulfate polyacrylamide gel electrophoresis (SDS-PAGE), followed by coomassie blue staining. To confirm the in vivo interaction between BCP and Pida4, Jurkat cells (10$^6$) were incubated with DMSO or 32 μg BCP in 2 ml RPMI medium at 37° C. for 24 hours. Total lysates were precipitated with streptavidin agarose bead and the precipitates underwent Western blot with anti-Pdia4 antibody or anti-Pdi andtibody. To detect the expression level of Pdia4 in cellular compartments, cytopalsmic, membrane and nuclear proteins of human CD4$^+$ T cells and Jurkat cells different cells were extracted according to the manufacturer's instruction (Chemicon, Calif., USA). Protein level of Pdia4 in primary and tumor cells. Total lysates (50 μg) of human CD4$^+$ T cells (pT), Jurkat cells E6.1, MCF-7, THP-1 and 293T cells underwent SDS-PAGE and Western blot with anti-Pdia4 antibody. After stripping, the same membrane was re-blotted with actin. To detect knockdown efficiency of Pdia4 and Hspa5, total lysates of lentivirally infecetd cells underwent Western blot with anti-Pdia4 and anti-Hspa5 antibodies. To examine the interaction between Pdia4 and Hspa5, 2×10$^7$ Jurkat cells were incubated with DSP at 4° C. for 24 hours. The lysates were precipitated with anti-Pdia4 antibody or control serum. The precipitates were separated by SDS PAGE. The membrane was blotted with ant-Hspa5 antibody. After stripping, the same membrane was blotted with ant-Pdia4 antibody.

In-Gel Digestion and Liquid Chromatography-Nanoelectrospray Ionization-Tandem Mass Spectrometery (LC-nanoESI-MS/MS) Analysis Band 1 were cut from the coomassie blue gel and subjected to in gel digestion. Briefly, the gel was dehydrated with acetonitrile, vacuum dried, and rehydrated with ammonium bicarbonate at 37° C. for 1 hour. After alkylation with iodoacetamide, the gel was suspended with 25 mM ammonium bicarbonate containing trypsin at 37° C. for 16 hours. Tryptic peptides were analyzed with LC-nanoESI-MS/MS system.

Briefly, the peptides were trapped and desalted isocratically on an LC-Packings PepMap™ C18 µ-Precolumn™ Cartidge (300 µm i.d.×5 mm; Dionex, Calif., USA) for 2 minutes with 0.1% formic acid. The peptides were separated on a C18 capillary column (15 cm×75 µm i.d.) packed with 5 µm, Zorbax 300 SB C18 paticles (Micro-Tech Scientific, Calif., USA), eluted using a 40 minute fast gradient of 5% to 80% acetonitrile containing 0.1% formic acid and subjected to Micromass Q-TOF Ultima™ API mass spectrometer, equipped with an ESI source. After data acquisition, MS/MS spectra for the sample were combined and querred against non-redundant protein database using Mascot program (Matrix Science, MA, USA). For MS/MS analysis of GST-Pdia4 and GST-Pdia4/CPA adduct, GST-Pdia4 (200 µg) was incubated with DMSO or CPA (24 µg) for 24 hours. The proteins underwent LC/MS/MS analysis.

Proteomic mass spectrometry analyses were performed by the Core Facilities for Proteomics Research, Academia Sinica.

Preparation and Pull Down Assay of GST Proteins pGEX4T3-Hspa5, pGEX4T3-Pdia4, and pGEX4T3-TecSH3 were obtained by cloning human Hspa5 cDNA, human Pdia4 cDNA and the SH3 domain of mouse Tec cDNA to a pGEX4T3 vector, respectively. GST fusion proteins were purified from the bacterial host $E.\ coli$ BL21 DE3 pLysS, which harbored the above constructs, according to the manufacturer's instructions (Amersham Biosciences, NJ, USA). Glutathione agarose bead-bound GST fusion proteins (0.15 µg) were incubated with DMSO vehicle or BCP (0.026 µg) for overnight. The proteins were separated by SDS-PAGE and blotted with avidin-POD. For competition assays, CP (0.16 µg (10-fold) and 0.81 µm (50-fold)) or CPA (0.09 µg (10-fold) and 0.45 µm (50-fold)) was added to the above incubation. For interference assay, 2-mercaptoethanol (2.2 mg) was added to the incubation. To test effect of CPA on disulfide isomerase activity of GST-Pdia4, reduced BPTI (0.39 µg) was incubated with redox buffer in the presence of vehicle, 5.64 µg GST-Pdia4 or 5.64 µg GST-Pdia4 plus CPA (0.33 µg). Enzymatic activity of GST-Pdia4, shown as fraction remaining (%), was determined by the conversion of the reduced BPTI into disulfide intermediates as described (Satoh, M., et al. (2005) *Cell Stress Chap.* 10(3), 211-220).

Quantification of PDI mRNAs Using Real-Time Reverse Transcription Polymerase Chain Reaction (RT-PCR)

Total RNAs from Jurkat cells were extracted using TRIZOL Reagent (Invitrogen) and converted into the first-stranded cDNAs using an Amersham Biosciences kit based on the manufacturer's instructions. Real-time PCR was performed by using 100 ng cDNA as a template with different sets of primers. The mRNA expressions of Pdia2, Pdi, Pdia3, Pdia4, Pdia5, Pdia6, Pdia13, Pdia15 and Pdia16 were normalized versus actin. Relative expression level (R.E.L.) is expressed as fold of Pdia2.

Confocal Microscopy

Jurkat cells were fixed with fixation buffer (Biolegend, Calif., USA). The cells were incubated with permeabilization buffer (Biolegend) containing 1 µg/ml anti-Pdia4 antibody for 0.5 hour. After washing, the cells were incubated with 0.5 µg/ml FITC-conjugated secondary antiserum. Alternatively, Jurkat cells were stained with BCP and FITC-conjugated avidin. The above cells were spread on slides and mounted with Prolong anti-Fade kit (Invitrogen). Confocal images were obtained using Zeiss LSM 510 microscopy.

Statistics

Data from three or more independent experiments were presented as mean±standard error (SE). Comparisons between multiple groups were made with ANOVA. $p<0.05$ was considered significant.

Example 2

CP and CPA Modulates Cell Growth of Acute Leukemia Jurkat T Cells

Some polyynes were reported to inhibit tumor cell growth (Dembitsky, V. M. (2006)*Lipids* 41(10), 883-924). CP, a linear chain polyyne, showed an inhibition of T cell proliferation (Chang, C. L., et al. (2007) *J. Immunol.* 178(11), 6984-6993) and its aglycone, CPA, promoted cell death of human umbilical vein endothelial cells (Wu, L. W., et al. (2007) *Planta Med.* 73(7), 655-661). In this example the effect of CP and CPA, two linear chain polyynes, on cell growth of Jurkat cells, a T cell line established from an acute leukemia patient (Weiss, A., et al. (1984) *J. Immunol.* 133(1), 123-128), were evaluated. It was found that CP and CPA inhibited cell growth of Jurkat cells, a T-ALL line, via inhibition of proliferation and/or promotion of cell death.

WST-1 assays showed that the half maximal inhibitory concentration ($IC_{50}$) of CP and CPA for growth inhibition of Jurkat cells was 52.8 and 2.5 µg/ml, respectively (Table 1). Cell growth was correlated with cell proliferation and survival/death. The effects of CP derivatives on Jurkat cells were then examined. Consistent with WST-1 data, CP and CPA inhibited Jurkat cell growth in a dose-dependent manner (FIG. 1A). At the low doses, CP (from 5 to 13.5 µg/ml) and CPA (from 0.7 to 1.3 µg/ml) inhibited Jurkat cell growth (FIG. 1A) but did not show significant cytotocxicity. In contrast, CP at 20 µg/ml or beyond and CPA at 2.5 µg/ml or beyond increased cell death of Jurkat cells to 10% or more (FIG. 1B).

The effects of the low doses of CP and CPA on cell proliferation of Jurkat cells were further tested. Both polyynes at the low doses significantly suppressed Jurkat cell proliferation, as evidenced by ASFE assays (FIG. 1C). Overall, the data showed that CP and CPA inhibited cell growth of Jurkat cells via suppression of cell proliferation at their low doses and promotion of cell death at their high doses. Consistently, CPA were found to induce cell death of TS/A, mammary gland carcinoma.

Example 3

Identification of Molecular Target of CP and CPA Using BCP

To better understand anti-growth mechanism of CP derivatives, molecular target(s) of CP derivatives were identified in this example.

Figure 3:
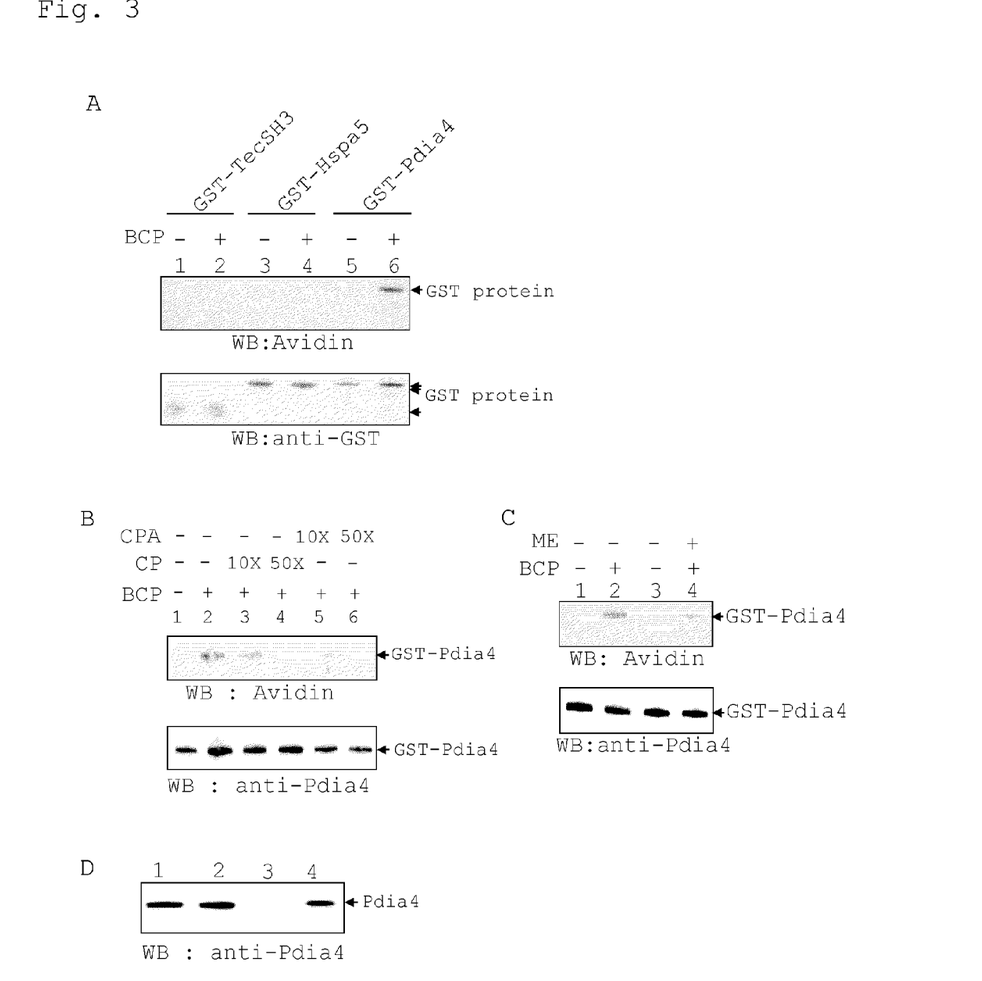

Biotinylated CP (BCP), a conjugate of biotin and CP, was used as a probe to identify the molecular target of CP derivatives in Jurkat cells. Conjugation of biotin to CP did not dramatically alter CP bioactivity, as evidenced by $IC_{50}$ of BCP and CP (Table 1). First, the BCP-bound protein(s) of Jurkat cells were characterized using Western blot. As shown in FIG. 2A, the protein(s) with 88 kD, designated as band 1, could interact with BCP (left panel, FIG. 2A). Consistently, band 1 appeared to be the most prominent protein(s) in the BCP precipitate as compared to the control precipitate in coomassie blue gel (right panel, FIG. 2A). However, a couple of extra protein bands appeared in the precipitate of both vehicle and BCP (right panel, FIG. 2A), which may be attributed to a lack of the pre-clearing step during precipitation. Next, the protein(s) of band 1 were characterized using the LC/MS/MS approach. Pdia4, a protein disulfide isomerase, and Hspa5, a glucose regulatory protein 78, were identified by proteomic analysis and database search to be the target of BCP (FIG. 2B). To further confirm whether BCP could directly bind Pdia4 and Hspa5, BCP was incubated in vitro with GST fusion proteins expressing TecSH3, an irrelevant protein, Pdia4 and Hspa5. Western blot data showed that GST-Pdia4 bound BCP to a greater extent (FIG. 3A). In contrast, GST-Hspa5 had a slight interaction with BCP, similar to GST-TecSH3. To test whether CP and CPA could bind Pdia4, excessive amount of CP and CPA was used to compete with BCP for GST-Pdia4 interaction. Competition assays indicated that CPA and CP could interfere with the interaction between BCP and GST-Pdia4 at a dose-dependent manner (FIG. 3B). CPA seemed to be more effective for the interference than CP. The data suggested that like BCP, CP and CPA could bind to Pdia4. In addition, 2-mercaptoethanol (ME), a reducing agent, significantly diminished the interplay of GST-Pdia4 and BCP (FIG. 3C), indicating an involvement of disulfide bond in this interplay.

The in vivo binding of BCP and Pdia4 were examined. Pdia4 was found to associate with BCP in Jurkat cells (FIG. 3D). The aforementioned data indicated that Hspa5 appeared in the BCP-bound protein complex (FIG. 2B-2C) but had a little, if any, binding affinity for BCP (FIG. 3A). This controversy suggests an association between Hspa5 and Pdia4. We confirmed that Pdia4 directly associated with Hspa5 in Jurkat cells (FIG. 3D). This association was also found in thyroid cells (Kuznetsov, G., Chen, L. B., and Nigam, S. K. (1994) *The Journal of biological chemistry* 269(37), 22990-22995). Overall, this example shows that CP and CPA directly bind to Pdia4 and that Hspa5 indirectly bound to BCP.

The above data were consistent with the previous findings indicating that Pdia4 complexed with other ER chaperones (Hspa5, Hsp90β1, etc.) (Kuznetsov, G., Chen, L. B., and Nigam, S. K. (1994) J. Biol. Chem. 269(37), 22990-22995; Feng, W., et al. (1995) The J. Biol. Chem. 270(20), 11851-11859; Vandenbroeck, K., et al. (2006) Cytokine 33(5), 264-273). As shown in (FIG. 5), Pdia4 and Hspa5 promoted cell growth of Jurkat cells. This example showed that Pdia4 could be a druggable target for cancer therapy and CP derivatives could be used as lead compounds for leukemia or other tumors.

Example 4

Covalent Binding and Inhibition of Enzymatic Activity of Pdia4 by CPA

The association of BCP and GST-Pdia4 or endogenous Pdia4 protein was intact in denaturing SDS gel and largely compromised in the presence of 2-mercaptoethanol (FIG. 3A-3D). To test the hypothesis that BCP covalently bound to GST-Pdia4 in a cysteine-related manner, MS/MS analysis was performed on the interplay between CPA, the most effective CP derivative, and GST-Pdia4 (FIG. 3E). Only one CPA adducted to two cysteine residues of the second CGHC motif of Pdia4 were found (FIG. 3E). However, it is possible that CPA can adduct to the first and third CGHC motifs to a lesser extent. To determine whether this covalent interaction affect disulfide isomerase activity of Pdia4. Reduced form of BPTI was used as Pdia4 substrate to test the enzymatic activity of GST-Pdia4. GST-Pdia4 showed disulfide isomerase activity as compared to GST protein in redox buffer as evidenced by a decrease in disulfide formation of bovine pancreatic trypsin inhibitor (left panel, FIG. 3F). Moreover, CPA inhibited this activity (right panel, FIG. 3F). The abovementioned data showed that CPA inhibited Pdia4 activity via its targeting to cysteine residues of CGHC active sites (FIG. 3F).

Example 5

Expression and Distribution of Pdia4 in T Cells and/or Other Cells

Pdia4 is the target of CP derivatives. To better understand biological significance of Pdia4, cellular distribution of Pdia4 in Jurkat cells was studied. Confocal images showed that Pdia4 was present in cytoplasm and membrane to a greater extent than in nucleus (FIG. 4A). Next, Pdia4 expression in Jurkat cells and primary cells were examined. As shown in FIG. 4B, Pdia4 was distributed in cytoplasmic, membrane and nuclear compartments, and the level of Pdia4 protein in Jutkat cells was higher than primary T cells (FIG. 4B). Consistently, the cytoplasmic level of Pdia4 protein was up-regulated in different types of tumor cells from 4- to 10-fold compared to primary $CD4^+$ T cells.

Example 6

Role of Pdia4 in Cell Growth, Proliferation and Death of Jurkat Cells

In this example, functional analysis of Pdia4 revealed its role implicated in cell growth, proliferation and activation of caspases 3/7 of Jurkat cells.

The function of Pdia4 in growth of Jurkat cells was investigated. GK cells, Jurkat cells infected with lentivirus expressing empty sequence, and A4 cells, Jurkat cells infected with lentivirus expressing Pdia4 RNAi sequence were generated. Protein level of Pdia4 in A4 cells was 20% that of Pdia4 in GK cells (left panel, FIG. 4C). Cell growth of GK and A4 cells were also compared. As shown in FIG. 4C, Pdia4 knockdown decreased cell growth of Jurkat cells by 200% (right panel FIG. 4C). To study the mechanism by which Pdia4 controlled cell growth, cell proliferation of control or knockdown Jurkat cells were tested using AFSE. Pdia4 knockdown significantly slowed down cell proliferation (FIG. 4D). In addition, activities of caspase 3 and caspase 7 were slightly increased in Jurkat cells with Pdia4 knockdown (FIG. 4E), implying that Pdia4 decrease induced cell death. The data shown above demonstrated that Hspa5 associates with Pdia4, indicating that Hspa5 and Pdia4 participate in the same pathway.

Cell growth of GK, A4, A5, Jurkat cells infected with lentirus expressing Hspa5 RNAi sequence, and A4/A5 cells, Jurkat cells co-infected with lentivirus expressing Pdia4 RNAi and Hspa5 RNAi were evaluated. As shown in FIG. 4F, double knockdown of Pdia4 and Hspa5 inhibited Jurkat cell growth more severely than either of single knockdown. The in vivo cell growths of Jurkat cells infected with empty sequence, or Pdia4 RNAi in SCID/beige mice were also investigated. The aforementioned data also show Pdia4 that promoted cell growth, cell proliferation and cell cycle to a greater extent than decreased cell death.

Although the present application has been described in detail above, it will be understood by one of ordinary skill in the art that various modifications can be made without departing from the spirit of the invention. Accordingly, the present application is limited only by the following claims. All cited patents, patent applications and publications referred to in this application are herein incorporated by reference in their entirety.

In the present application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

As will be appreciated by one of skill in the art, while the present specification may simply use one of the terms "comprise," "consists," or "consists essentially of," this is simply a shorthand way of describing all three possibilities, unless otherwise specified or unless the term is used in the claim (in which case the terms will have their normally accepted meanings under claim interpretation). Thus, as the terms are used above, they designate all three possibilities, unless explicitly noted otherwise

What is claimed is:

1. A method for inhibiting growth, proliferation and/or inducing death of protein disulfide isomerase a4 (Pdia4)-overexpressed cancer cells, comprising
(a) detecting the presence of the Pdia4-oveprxpressed cancer cells in a subject with cancer; and
(b) administering to the subject with the detected presence of the Pdia4-overexpressed cancer cells a Pdia4 inhibitor in a therapeutically effective amount for inhibiting the growth, proliferation and/or inducing the death of the Pdia4-overexpressed cancer cells in the subject with the cancer, wherein the Pdia4 inhibitor is selected from the group consisting of cytopiloyne, cytopiloyne aglycone, biotinylated cytopiloyne, an Pdia4 anti-sense small interfering RNA (siRNA), and an anti-Pdia4 short hairpin RNA (shRNA).

2. The method of claim 1, wherein the Pdia4-overexpressed cancer cells are of a T cell acute lymphocytic leukemia or a mammary gland carcinoma.

3. The method of claim 1, wherein the Pdia4 inhibitor inhibits expression of Pdia4 mRNA and/or Pdia4 protein.

4. The method of claim 1, wherein the Pdia4 inhibitor binds to and inhibits the catalytic activity of the Pdia4 protein in the Pdia4-overexpressed cancer cells but does not bind to or inhibit other protein disulfide isomerases.

5. The method of claim 1, wherein the cancer cell is at least one selected from the group consisting of leukemia, breast cancer, liver cancer, renal cancer, lung cancer, melanoma cancer, and colon cancer.

6. The method of claim 1, wherein the siRNA comprises a nucleotide sequence selected from the group consisting of SEQ ID NOs: 1-3.

7. The method of claim 1, wherein the detecting step is performed with an antibody to Pdia4 on a biological sample obtained from the subject with the cancer.

8. A method for inhibiting growth, proliferation and/or inducing death of Pdia4-overexpressed cancer cells, comprising:
administering to a subject afflicted with the Pdia4-overexpressed cancer cells a Pdia4 inhibitor in a therapeutically effective amount for inhibiting the growth, proliferation and/or inducing the death of the Pdia4-overexpressed cancer cells in the subject, wherein the Pdia4 inhibitor is selected from the group consisting of cytopiloyne, cytopiloyne aglycone, biotinylated cytopiloyne, an Pdia4 anti-sense small interfering RNA (siRNA), and an anti-Pdia4 short hairpin RNA (shRNA).

9. The method of claim 8, wherein the cancer cell is at least one selected from the group consisting of leukemia, breast cancer, liver cancer, renal cancer, lung cancer, melanoma cancer, and colon cancer.

10. The method of claim 8, wherein the siRNA comprises a nucleotide sequence selected from the group consisting of SEQ ID NOs: 1-3.

11. The method of claim 8, prior to the administering step further comprising detecting the presence of Pdia4 mRNA or Pdia4 protein in a biological sample from the subject afflicted with the Pdia4-overexpressed cancer cells.

12. The method of claim 11, wherein the detecting step is performed with an anti-Pdia4 antibody-staining of the Pdia4-overexpressed cancer cells in the biological sample from the subject.

13. The method of claim 8, wherein the Pdia4 inhibitor binds to and inhibits the catalytic activity of the Pdia4 protein but does not bind to or inhibit other protein disulfide isomerases of the Pdia4-overexpressed cancer cells.

14. The method of claim 8, wherein the Pdia4-overexpressed cancer cells are of a T cell acute lymphocytic leukemia or a mammary gland carcinoma.

15. A method for inhibiting growth and/or metastasis of a Pdia4-overexpressed tumor, comprising:
administering to a subject afflicted with the Pdia4-overexpressed tumor a Pdia4 inhibitor in an amount effective for inhibiting the growth and/or metastasis of the Pdia4-overexpressed tumor in the subject, wherein the Pdia4 inhibitor is selected from the group consisting of cytopiloyne, cytopiloyne aglycone, biotinylated cytopiloyne, an Pdia4 anti-sense small interfering RNA (siRNA), and an anti-Pdia4 short hairpin RNA (shRNA).

16. The method of claim 15, wherein the cancer cell is at least one selected from the group consisting of leukemia, breast cancer, liver cancer, renal cancer, lung cancer, melanoma cancer, and colon cancer.

* * * * *

SEQUENCE LISTING

```
<160> NUMBER OF SEQ ID NOS: 10

<210> SEQ ID NO 1
<211> LENGTH: 58
<212> TYPE: RNA
<213> ORGANISM: Artificial Sequence
<220> FEATURE:
<223> OTHER INFORMATION: siRNA

<400> SEQUENCE: 1
ccgggcuugu guugaccaaa gagaacucga guucucuuug gucaacacaa gcuuuuug         58

<210> SEQ ID NO 2
<211> LENGTH: 58
<212> TYPE: RNA
<213> ORGANISM: Artificial Sequence
<220> FEATURE:
<223> OTHER INFORMATION: siRNA

<400> SEQUENCE: 2
ccggccaaga aguacaaggg ccaaacucga guuuggcccu uguacuucuu gguuuuug         58

<210> SEQ ID NO 3
<211> LENGTH: 58
<212> TYPE: RNA
<213> ORGANISM: Artificial Sequence
<220> FEATURE:
<223> OTHER INFORMATION: siRNA

<400> SEQUENCE: 3
ccgggcaagg ugucaaacga ugcuacucga guagcaucgu uugacaccuu gcuuuuug         58

<210> SEQ ID NO 4
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 4
ccgggcttgt gttgaccaaa gagaactcga gttctctttg gtcaacacaa gctttttg         58
```

<210> SEQ ID NO 5
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 5
ccggccaaga agtacaaggg ccaaactcga gtttggccct tgtacttctt ggtttttg    58

<210> SEQ ID NO 6
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 6
ccgggcaagg tgtcaaacga tgctactcga gtagcatcgt ttgacacctt gcttttttg    58

<210> SEQ ID NO 7
<211> LENGTH: 5
<212> TYPE: PRT
<213> ORGANISM: Homo sapiens

<400> SEQUENCE: 7

Lys Cys His Gly Cys
1               5

<210> SEQ ID NO 8
<211> LENGTH: 4
<212> TYPE: PRT
<213> ORGANISM: Homo sapiens

<400> SEQUENCE: 8

Asn Asp Ala Asp
1

<210> SEQ ID NO 9
<211> LENGTH: 13
<212> TYPE: PRT
<213> ORGANISM: Homo sapiens

<400> SEQUENCE: 9

Ile Ile Asp Ala Asp Asn Val Val Glu Asp Phe Asn Glu
1               5                   10

<210> SEQ ID NO 10
<211> LENGTH: 14
<212> TYPE: PRT
<213> ORGANISM: Homo sapiens

<400> SEQUENCE: 10

Ile Leu Val Glu Phe Tyr Ala Pro Trp Cys Gly His Cys Lys
1               5                   10